United States Patent

Ono et al.

[11] Patent Number: 6,077,983
[45] Date of Patent: Jun. 20, 2000

[54] METHOD FOR REACTIVATING RUTHENIUM CATALYST

[75] Inventors: Mitsuji Ono, Kojima-Gun; Masashi Nonaka, Kurashiki, both of Japan

[73] Assignee: Asahi Kasei Kogyo Kabushiki Kaisha, Tokyo, Japan

[21] Appl. No.: 09/068,204

[22] PCT Filed: Oct. 18, 1996

[86] PCT No.: PCT/JP96/03026

§ 371 Date: Apr. 30, 1998

§ 102(e) Date: Apr. 30, 1998

[87] PCT Pub. No.: WO97/16249

PCT Pub. Date: May 9, 1997

[30] Foreign Application Priority Data

Nov. 1, 1995 [JP] Japan ................................. 7-284911

[51] Int. Cl.$^7$ ................................. C07C 5/11; B01J 23/96
[52] U.S. Cl. ........................... 585/269; 585/273; 502/22; 502/38; 502/50; 502/53
[58] Field of Search .................................. 585/269, 273; 502/22, 38, 50, 53

[56] References Cited

U.S. PATENT DOCUMENTS 3,966,636 6/1976 Jenkins et al. ........................ 252/419
5,206,194 4/1993 Clark ........................................ 502/26
5,391,527 2/1995 Kojima et al. .......................... 502/53

FOREIGN PATENT DOCUMENTS

| 0 037 137 | 10/1981 | European Pat. Off. . |
| 0 552 809 | 7/1993 | European Pat. Off. . |
| 60-255738 | 12/1985 | Japan . |
| 62-65751 | 3/1987 | Japan . |
| 62-67033 | 3/1987 | Japan . |
| 1-159059 | 6/1989 | Japan . |
| 3-68453 | 3/1991 | Japan . |
| 7-178341 | 7/1995 | Japan . |

*Primary Examiner*—Walter D. Griffin
*Assistant Examiner*—Tam M. Nguyen
*Attorney, Agent, or Firm*—Pennie & Edmonds LLP

[57] ABSTRACT

A method for recovering the activity of a ruthenium catalyst which comprises a step of bringing a ruthenium catalyst decreased in activity by its use in hydrogenation of an unsaturated organic compound into contact with oxygen in a liquid phase, and a step of maintaining the catalyst at a hydrogen partial pressure lower than that at the hydrogenation and a temperature not lower than a temperature lower by 50° C. than the hydrogenation temperature.

16 Claims, No Drawings

METHOD FOR REACTIVATING RUTHENIUM CATALYST

TECHNICAL FIELD

The present invention provides a method for effectively utilizing a ruthenium catalyst to be used in hydrogenating an unsaturated organic compound. More particularly, the present invention relates to a method for recovering the activity of a ruthenium catalyst decreased by its repeated or continuous use in hydrogenation.

BACKGROUND ART

Ruthenium catalysts are used in hydrogenation of unsaturated organic compounds, hydrogenation of olefins, ketones, aldehydes, etc. and, in particular, hydrogenation or partial hydrogenation of the nuclei of aromatic compounds by taking advantage of the high activity and specific reaction selectivity of the ruthenium catalysts.

In general, typical examples of cause for the decrease in activity of a catalyst used in hydrogenating an unsaturated organic compound are a physical change of the active site of the catalyst itself caused by reaction circumstances such as reaction temperature and reaction heat (e.g. sintering), or the accumulation of a catalytic poison (e.g. a sulfur compound or a foreign metal). In order to avoid these causes, some measure for controlling the reaction temperature or preventing contamination with the catalytic poison is widely and industrially taken.

The same activity decrease phenomenon as above occurs in the case of ruthenium catalysts. In particular, as to the decrease of their activity caused by a catalytic poison, JP-A-60-255738 describes an example of poisoning by a sulfur compound, and JP-A-62-67033 describes poisoning by iron. JP-A-62-65751 discloses an example of method for regenerating a ruthenium catalyst poisoned by a sulfur compound.

However, it has been confirmed that a ruthenium catalyst repeatedly or continuously used in hydrogenating an unsaturated organic compound has a decreased activity which is considered to be due to a cause utterly different from the above-mentioned physical change or poisoning of the catalyst. Although theoretically clear explanation of this phenomenon is difficult, it can be speculated that the amount of some reaction inhibitor produced by the interaction between hydrogen and the ruthenium catalyst increases with the lapse of time under the reaction conditions, for example, because an activity decrease larger than that estimated from the physical change and poisoned condition of the catalyst is observed and the reaction is carried out in the presence of hydrogen.

As a method for recovering the ruthenium catalyst activity decreased by the above cause, JP-A-1-159059 discloses a method of bringing the ruthenium catalyst into contact with oxygen in a liquid phase, and JP-A-3-68453 discloses a method of maintaining the catalyst at a hydrogen partial pressure lower than that at the hydrogenation and a temperature not lower than a temperature lower by 50° C. than the hydrogenation temperature.

However, although these conventional methods are effective when the decrease rate of the activity relative to the initial activity is low, they are not sufficiently effective for a ruthenium catalyst decreased in activity to 60% or less of the initial activity by repeated or continuous use. Therefore, there is desired a more effective method for recovering the activity of such a ruthenium catalyst.

JP-A-7-178341 discloses a method comprising heat-treating a silica-supported ruthenium catalyst used in hydrogenation at a temperature of 60° C. or higher in an oxygen-containing gas and then at a temperature of 20–200° C. in a hydrogen-containing gas, but does not describe the regeneration of a ruthenium catalyst in a liquid phase.

DISCLOSURE OF INVENTION

The present invention provides a method for efficiently recovering the activity of a ruthenium catalyst decreased, in particular decreased to 60% or less of the initial activity, by the interaction between hydrogen and the ruthenium catalyst, to make the reuse of the catalyst possible.

The present invention is a method for recovering the activity of a ruthenium catalyst which comprises a step of bringing a ruthenium catalyst decreased in activity by its use in hydrogenation of an unsaturated organic compound into contact with oxygen in a liquid phase, and a step of maintaining the catalyst at a hydrogen partial pressure lower than that at the hydrogenation and a temperature not lower than a temperature lower by 50° C. than the hydrogenation temperature. According to the method of the present invention, for example, the activity of a ruthenium catalyst decreased to 60% or less of the initial activity can be sufficiently recovered, so that the catalyst can be very effectively reused.

BEST MODE FOR CARRYING OUT THE INVENTION

The ruthenium catalyst of interest in the present invention includes ruthenium catalysts which are used in hydrogenation of unsaturated organic compounds, hydrogenation of olefins, ketones, aldehydes, etc. and, in particular, hydrogenation or partial hydrogenation of the nuclei of aromatic compounds, and comprise, as a metal component(s), ruthenium alone or a combination of ruthenium and other metals. The metal component(s) of the ruthenium catalyst may be supported on a suitable carrier. In the hydrogenation, a part of or the whole of ruthenium is in a reduced state, i.e., a metallic state. Specific examples of the ruthenium catalyst are ruthenium black, metallic ruthenium fine particles having a very small average crystallite diameter (for example, tens to hundreds angstroms), catalysts obtained by incorporating other metals or compounds thereof into ruthenium black or the metallic ruthenium fine particles, catalysts obtained by supporting ruthenium on a suitable carrier and the like. The carrier includes various metal oxides (e.g. silica, silica-alumina, alumina, zirconia, hafnia, chromia, titania, iron oxide, cobalt oxide, niobium oxide, gallium oxide, tantalum oxide, rare earth oxides and zinc oxide), inorganic salts, activated carbon, resins, etc.

Hydrogenation with the ruthenium catalyst is usually carried out at a hydrogen pressure of 1 to 200 kg/cm$^2$G and a reaction temperature of room temperature to about 250° C. It is known that the ruthenium catalyst used in the hydrogenation for a long period of time usually has a decreased activity. The decrease of the activity is caused by influence of, for example, the physical change of the catalyst itself or the accumulation of a catalytic poison. The degree of the activity decrease is dependent on the reaction conditions, in particular, the temperature and the hydrogen pressure. The activity decrease, however, proceeds gradually also under reaction circumstances or conditions under which the presence of the above-mentioned influence is not conceivable. It can be speculated that the activity decrease corresponds to an increase with the lapse of time of some reaction inhibitor produced by the interaction between hydrogen and the ruthenium catalyst. Such a phenomenon could be confirmed only by careful observation of the catalytic activity for a long period of time. In particular, there has been no simple and preferable method for efficient regeneration of a catalyst decreased in activity to 60% or less of the initial activity.

According to the method of the present invention, a ruthenium catalyst decreased in activity, in particular, decreased in activity to 60% or less of the initial activity can be surprisingly greatly recovered in activity by a very simple method comprising a combination of a step of bringing the ruthenium catalyst into contact with oxygen in a liquid phase, and a step of maintaining the catalyst at a hydrogen partial pressure lower than that at the hydrogenation and a temperature not lower than a temperature lower by 50° C. than the hydrogenation temperature.

The term "activity" used here means the amount of a reactant converted per unit weight of the catalyst in a definite reaction time under the same reaction conditions.

Although the state of the liquid phase in the step of bringing the catalyst into contact with oxygen in the liquid phase may be either a state in which the ruthenium catalyst is dispersed in a suitable liquid to form a slurry, or a state in which the ruthenium catalyst is impregnated with a liquid, at least the surface of the catalyst should be covered with a liquid. Any liquid may be used so long as it has no undesirable influence on the catalyst or its carrier. Specific examples of such a liquid are water, alcohols and hydrocarbons. Preferable examples thereof are water and alcohols. Water is most preferable so long as the catalyst is not water-soluble. In this case, water may contain other water-soluble compounds such as salts of various metals or organic substances so long as they have no undesirable influence on the catalyst.

When the catalyst is brought into contact with oxygen in the liquid phase, there can be used as an oxygen source a gas containing molecular oxygen, such as oxygen gas or air, or a compound capable of generating nascent oxygen, such as hydrogen peroxide, sodium hypochlorite. Oxygen gas is preferably used as it is or after being diluted with a suitable inert gas because such an operation is easy.

The oxygen concentration of the liquid phase is $1 \times 10^{-7}$ to 1 Nml/ml, preferably $1 \times 10^{-5}$ to 0.1 Nml/ml, in terms of oxygen gas in standard state. N (normal) herein means that unit is based on gas in standard state. When the oxygen concentration is less than $1 \times 10^{-7}$ Nml/ml, a treatment for a very long period of time is undesirably required for recovering the activity. When the oxygen concentration is more than 1 Nml/ml, an irreversible change of the catalyst is undesirably caused in some cases by rapid oxidation of ruthenium on the catalyst surface.

When the liquid phase is a slurry, the oxygen source may be directly supplied to the liquid phase. When the liquid phase is in a state obtained by impregnation in which the volume of the liquid is small, the oxygen source may be supplied together with vapor of the liquid. When an alcohol or a hydrocarbon is used as the liquid, there is chosen an oxygen concentration which is unlikely to cause inflammation or explosion. The most preferable method for supplying the oxygen source is dispersing the ruthenium catalyst in water and then supplying an oxygen-containing gas to the resulting dispersion. This method requires only an easy procedure and hence is preferable.

The operations for recovering the activity of the ruthenium catalyst can be carried out under reduced pressure or at atmospheric pressure or under pressure. Pressurizing may be conducted for increasing the oxygen concentration of the liquid phase. Although the operating temperature at which the catalyst is brought into contact with oxygen varies depending on the liquid used, it is 0–300° C., preferably 30–200° C., more preferably 50–150° C. The operating time may be properly determined depending on the degree of decrease in activity of a catalyst to be treated and the desired degree of recovery of the activity, and is usually several minutes to several days.

The procedure of maintaining the catalyst at a hydrogen partial pressure lower than that at the hydrogenation and a temperature not lower than a temperature lower by 50° C. than the hydrogenation temperature can be carried out in either a gas phase or a liquid phase. The hydrogen partial pressure employed in the method of the present invention may be any pressure so long as it is lower than a hydrogen partial pressure at the hydrogenation. It, however, is preferably one-half or less of the hydrogen partial pressure at the hydrogenation, more preferably zero or near zero because when the difference between the two hydrogen partial pressures is not sufficient, the recovery of the activity requires a long period of time in some cases. The operating temperature at which the catalyst is maintained is not lower than a temperature lower by 50° C. than, preferably not lower than a temperature lower by 40° C. than, more preferably not lower than a temperature lower by 30° C. than, the hydrogenation temperature. The operating temperature may be higher than the hydrogenation temperature. However, when the temperature is too high, an irreversible change is caused in the active site of the catalyst in some cases. Therefore, it is preferable to choose the upper limit of the temperature which is suitable for characteristics of the catalyst. In the case of metallic ruthenium fine particles to be used as a catalyst for partial hydrogenation of an aromatic hydrocarbon, for example, it is preferable to maintain the catalyst at a temperature not higher than 250° C., preferably not higher than 200° C., for preventing the physical change in properties of the catalyst. On the other hand, when the operating temperature is lower than a temperature lower by 50° C. than the hydrogenation temperature, a treatment for a very long period of time is required for recovering the activity. Therefore, such a temperature is not practical. The maintaining time in such a procedure for recovering the activity may be properly determined depending on the degree of decrease in activity of a catalyst to be treated and the desired degree of recovery of the activity, and is usually several minutes to several days.

There may be carried out at first either the step of bringing the catalyst into contact with oxygen in a liquid phase, or the step of maintaining the catalyst at a hydrogen partial pressure lower than that at the hydrogenation and a temperature not lower than a temperature lower by 50° C. than the hydrogenation temperature. It is preferable to carry out at first the step of bringing the catalyst into contact with oxygen in a liquid phase.

For carrying out the above-mentioned operations for recovering the activity, it is preferable that organic substances derived from the hydrogenation and present together with the ruthenium catalyst are previously separated and removed from the ruthenium catalyst. The organic substances present together with the ruthenium catalyst refer to, for example, a starting unsaturated organic substance, a reaction product, by-products produced depending on the reaction, a solvent impurities and the like.

The method for recovering the activity of the catalyst of the present invention can be practiced by a batchwise operation or continuously. The ruthenium catalyst restored in activity can be reused for reaction after being properly washed, dried and then formed into a preferable shape.

As reactions for which the catalyst restored in activity is reused, hydrogenation of unsaturated organic compounds and the like are mentioned. As unsaturated organic compounds, there are used olefins, ketones, aldehydes, aromatic compounds and the like. The catalyst restored in activity is preferably used in hydrogenation of aromatic compounds, more preferably in reactions for producing cycloolefins by partial hydrogenation of single-ring aromatic hydrocarbons. As the single-ring aromatic hydrocarbons herein, for example, benzene, toluene, o-, m-, p-xylene, ethylbenzene and the like are preferably mentioned.

Preparation of a Ruthenium Catalyst (a hydrogenation catalyst) Decreased in Activity Which is to be Used in Examples Into a tank flow reactor equipped with an oil separating tank as attached tank and having a Teflon-coated inner surface were charged 1 part by weight of a ruthenium catalyst composed mainly of metallic ruthenium fine particles obtained by reducing ruthenium previously incorporated with zinc, 7 parts by weight of zirconium oxide powder and 160 parts by weight of a 18 wt % aqueous zinc sulfate ($ZnSO_4.7H_2O$) solution. Partial hydrogenation of benzene was continuously carried out at 150° C. under a hydrogen pressure of 50 kg/cm²G while feeding benzene containing no catalytic poison such as sulfur, at a rate of 140 parts by weight per hour. In this case, the composition of the aqueous phase containing the catalyst in the reaction system was always kept constant and the reaction product consisting of benzene, cyclohexene and cyclohexane was continuously taken out of the oil separating tank.

A portion of the ruthenium catalyst was taken out of the reactor 1,000 hours and 2,000 hours after the start of the flow and charged into an autoclave having an internal volume of 1 liter and a Teflon-coated inner surface. The oily layer was separated and the gas phase was replaced with hydrogen. After the temperature was raised to 150° C., 140 ml of benzene was injected into the autoclave and batchwise hydrogenation was carried out with stirring at 150° C. for 15 minutes while supplying hydrogen so as to maintain the total pressure at 50 kg/cm²G. Thus, the activity was evaluated.

The initial activity of the ruthenium catalyst was evaluated by carrying out batchwise hydrogenation by the use of the same catalyst as that used for the above-mentioned flow reaction. The results obtained are shown in Table 1. The activity was decreased with the lapse of time to less than 60% of the initial activity after 1,000 hours and less than 50% of the initial activity after 2,000 hours.

EXAMPLE 1 (present invention)

A portion of the ruthenium catalyst decreased in activity by its use in the hydrogenation for 2,000 hours in the aforesaid flow reactor was taken out of the reactor and charged into an autoclave having an internal volume of 1 liter and a Teflon-coated inner surface. After the oil layer was separated, a procedure for recovering the activity was carried out. Air diluted with nitrogen to an oxygen concentration of 3 vol % was blown through the catalyst at a flow rate of 10 Nl/hr to treat the catalyst at a temperature of 80° C. for 30 minutes. Then, the air supply was stopped and the inner atmosphere of the autoclave was replaced with nitrogen (oxygen partial pressure: zero). Thereafter, the temperature was raised to 150° C. while keeping the autoclave hermetically sealed, and the catalyst was held in such a condition for 4 hours. After rapid cooling, the same batchwise hydrogenation as described above was carried out to find that a reaction product composed of 44 benzene, 46 cyclohexene and 10 cyclohexane by weight ratio was obtained. The evaluation results of the activity of the catalyst are shown in Table 2.

EXAMPLE 2 (comparison)

A portion of the ruthenium catalyst decreased in activity by its use in the hydrogenation for 1,000 hours in the aforesaid flow reactor was taken out of the reactor and charged into an autoclave having an internal volume of 1 liter and a Teflon-coated inner surface. After the oil layer was separated, a procedure for recovering the activity was carried out. Air diluted with nitrogen to an oxygen concentration of 3 vol % was blown through the catalyst at a flow rate of 10 Nl/hr to treat the catalyst at a temperature of 80° C. for 30 minutes. The air supply was stopped and after rapid cooling, batchwise hydrogenation was carried out in the same manner as in Example 1, whereby the activity of the catalyst was evaluated. The results obtained are shown in Table 2.

EXAMPLE 3 (comparison)

A portion of the ruthenium catalyst decreased in activity by its use in the same hydrogenation for 1,000 hours as in Example 2 was taken out of the reactor and charged into an autoclave having an internal volume of 1 liter and a Teflon-coated inner surface. After the oil layer was separated, a procedure for recovering the activity was carried out. The inner atmosphere of the autoclave was replaced with nitrogen, after which the temperature was raised to 150° C. while keeping the autoclave hermetically sealed, and the catalyst was held in such a condition for 4 hours. After rapid cooling, batchwise hydrogenation was carried out in the same manner as in Example 1, whereby the activity of the catalyst was evaluated. The results obtained are shown in Table 2.

EXAMPLE 4 (comparison)

A portion of the ruthenium catalyst decreased in activity by its use in the same hydrogenation for 1,000 hours as in Example 2 was taken out of the reactor, separated by filtration, washed with water and then dried in vacuo at a temperature of 80° C. for 4 hours to be freed of water completely. Thereafter, a procedure for recovering the activity was carried out. First, the dried catalyst was charged into a regenerator made of heat-resistant glass, and air diluted with nitrogen to an oxygen concentration of 3 vol % was blown through the catalyst at a flow rate of 10 Nl/hr to treat the catalyst at a temperature of 80° C. for 30 minutes. Then, the air supply was stopped, followed by rapid cooling. The catalyst was taken out of the regenerator and a 18 wt % aqueous zinc sulfate ($ZnSO_4.7H_2O$) solution 20 times as much as the catalyst was added. The resulting mixture was charged into an autoclave having an internal volume of 1 liter and a Teflon-coated inner surface, and the inner atmosphere of the autoclave was replaced with nitrogen (oxygen partial pressure: zero). Then, the temperature was raised to 150° C. while keeping the autoclave hermetically sealed, and the catalyst was held in such a condition for 4 hours. After rapid cooling, the same batchwise hydrogenation as described above was carried out, whereby the activity of the catalyst was evaluated. The results obtained are shown in Table 2.

TABLE 1

Catalytic activity for batchwise
hydrogenation (reaction time: 15 min)

| Flow reaction time | Initial catalyst | 1,000 hrs | 2,000 hrs |
| --- | --- | --- | --- |
| Amount of benzene converted | 34.2 g | 18.7 g | 15.2 g |

TABLE 2

Catalytic activity for batchwise
hydrogenation (reaction time: 15 min)

| | | Example 1 (present invention) | Example 2 (comparison) | Example 3 (comparison) | Example 4 (comparison) |
| --- | --- | --- | --- | --- | --- |
| Amount of benzene converted | Before regeneration | 15.2 g | 18.7 g | 18.7 g | 18.7 g |
| | After regeneration | 33.4 g | 20.5 g | 20.8 g | 18.9 g |

INDUSTRIAL APPLICABILITY

By the present invention, a ruthenium catalyst decreased in activity to, in particular, 60% or less of the initial activity by its use in hydrogenation of an unsaturated organic compound can be markedly restored in activity with great ease without causing a physical change in properties of the catalyst itself, so that the expensive ruthenium catalyst can be efficiently reused.

We claim:

1. A method for producing a cycloolefin by partially hydrogenating a single-ring aromatic hydrocarbon in the presence of a ruthenium catalyst, which comprises the steps of
    bringing the ruthenium catalyst, whose activity has decreased in the hydrogenation, into contact with oxygen in a liquid phase, wherein the catalyst is dispersed in or impregnated with a liquid;
    maintaining the catalyst at a hydrogen partial pressure lower than that at the hydrogenation and at a temperature not lower than a temperature lower by 50° C. than the hydrogenation temperature to obtain a ruthenium catalyst restored in activity; and
    partially hydrogenating the single-ring aromatic hydrocarbon in the presence of the ruthenium catalyst restored in activity.

2. A method for producing a cycloolefin according to claim 1, wherein the step of bringing the ruthenium catalyst into contact with oxygen in a liquid phase is carried out before the step of maintaining the catalyst at a hydrogen partial pressure lower than that at the hydrogenation and at a temperature not lower than a temperature lower by 50° C. than the hydrogenation temperature.

3. A method for producing a cycloolefin according to claim 1, wherein organic substances derived from said hydrogenation are previously separated from the ruthenium catalyst.

4. A method for producing a cycloolefin according to claim 2, wherein organic substances derived from said hydrogenation are previously separated from the ruthenium catalyst.

5. A method for producing a cycloolefin according to claim 1, wherein the activity of the ruthenium catalyst decreased by its use in said hydrogenation is 60% or less of the initial activity.

6. A method for producing a cycloolefin according to claim 2, wherein the activity of the ruthenium catalyst decreased by its use in said hydrogenation is 60% or less of the initial activity.

7. A method for producing a cycloolefin according to claim 3, wherein the activity of the ruthenium catalyst decreased by its use in said hydrogenation is 60% or less of the initial activity.

8. A method for producing a cycloolefin according to claim 4, wherein the activity of the ruthenium catalyst decreased by its use in said hydrogenation is 60% or less of the initial activity.

9. A method for producing a cycloolefin according to claim 1, wherein said single-ring aromatic hydrocarbon is benzene.

10. A method for producing a cycloolefin according to claim 2, wherein said single-ring aromatic hydrocarbon is benzene.

11. A method for producing a cycloolefin according to claim 3, wherein said single-ring aromatic hydrocarbon is benzene.

12. A method for producing a cycloolefin according to claim 4, wherein said single-ring aromatic hydrocarbon is benzene.

13. A method for producing a cycloolefin according to claim 5, wherein said single-ring aromatic hydrocarbon is benzene.

14. A method for producing a cycloolefin according to claim 6, wherein said single-ring aromatic hydrocarbon is benzene.

15. A method for producing a cycloolefin according to claim 7, wherein said single-ring aromatic hydrocarbon is benzene.

16. A method for producing a cycloolefin according to claim 8, wherein said single-ring aromatic hydrocarbon is benzene.

* * * * *